United States Patent [19]

Qureshi et al.

[11] Patent Number: 5,183,765

[45] Date of Patent: Feb. 2, 1993

[54] MEANS AND METHOD OF MEASURING AND DISPENSING

[75] Inventors: Humayun Qureshi, Wayland; Donald Schwartz, Marblehead, both of Mass.

[73] Assignee: DRD Diluter Corporation, Danvers, Mass.

[21] Appl. No.: 595,975

[22] Filed: Oct. 11, 1990

[51] Int. Cl.⁵ ............................................... B01L 3/02
[52] U.S. Cl. .................................. 436/180; 222/282; 222/309; 422/100
[58] Field of Search .............. 436/180, 174; 422/100, 422/103; 222/282, 309, 14, 64, 135

[56] References Cited

U.S. PATENT DOCUMENTS

| | | | |
|---|---|---|---|
| 4,237,094 | 12/1980 | Souvaniemi et al. | 422/103 |
| 4,457,184 | 7/1984 | Shiono | 422/100 |
| 4,484,698 | 11/1984 | Starr | 222/14 |
| 4,838,999 | 6/1989 | Haar et al. | 422/100 |
| 5,015,591 | 5/1991 | Meyrat et al. | 422/100 |

FOREIGN PATENT DOCUMENTS 56-65344 12/1981 Japan.
1-284761 11/1989 Japan.

Primary Examiner—Jill A. Johnston
Attorney, Agent, or Firm—Wolf, Greenfield & Sacks

[57] ABSTRACT

A method of metering and dispensing a first liquid, using a probe having an aspiration tip defining a tip chamber. The aspiration tip chamber is sized so as to be capable of holding and metering at least two largely different volumes of a first liquid. In the method a filler liquid is introduced into a portion of the chamber and a first liquid is aspirated in a predetermined amount into the chamber, so that a predetermined amount of the first liquid can be metered and dispensed with high accuracy and precision. The chamber is capable of being used for two largely different doses of the first liquid. Additional liquids can be aspirated along with the filler liquid. The filler using can be a reactant, a cleaner or the like.

13 Claims, 1 Drawing Sheet

MEANS AND METHOD OF MEASURING AND DISPENSING

BACKGROUND OF THE INVENTION

Many aspirating diluter/dispenser devices are known. Such devices often have a hand held probe which is used as a pipette to measure predefined amounts of a sample, then dilute that sample with a predefined amount of a reagent and finally dispense the reagent and/or sample, after having accomplished reasonably accurate and precise measurement of the sample and/or the sample and reagent. Such devices often use replacable tips which contain chambers carrying the reagent and/or sample so as to space the samples from a central liquid supply in the chamber. Often a variety of tips having different sized chambers are used to meter and dispense different volumes of a sample.

The different sized tips are required, since the devices are aspirating devices and if large air spaces are left in a tip when measuring small quantities for example, this can introduce errors in measurement and/or give difficulty in aspirating and dispensing.

Thus, it is well known that a dead air space between a vacuum or positive pressure creating mechanism, like a syringe or a piston, can cause an increase in liquid volume pickup or delivery. For this reason, sampling tips or tubes on probes are designed to be filled with liquid sample and/or reagent used to eliminate large air spaces, since liquid is, for all practical purposes, incompressible, unlike gases such as air.

Conventional disposable tips are often formed of plastic and made disposable to avoid contamination between one sample and another. It is often desired that the sample is picked up and confined to the disposable tip so that no sample actually gets into a hand held probe used in measuring and dispensing devices, to eliminate possible contamination of the device.

The need for contamination elimination is particularly important in many medical applications, particularly with AIDS or other virus tests and with sensitive tests such as nucleaic acid tests and determinations.

Often very small sample volumes down to one microliter and less, are measured and dispensed in laboratory testings. Often such small samples are diluted with reagents in much larger volumes. It has been difficult to use a standard size, single size disposable tip to handle both the sample and reagent, since often a tip that is large enough to hold reagent and large sample volume will have a dead air space that can cause considerable error in a small sample If the sample size is varied, as from 1 microliter to perhaps 50 microliters in different tests or different procedures, that difference can cause the dead air space to be a problem.

SUMMARY OF THE INVENTION

It is an object of this invention to provide a means and method for measuring and dispensing liquids with accuracy and percision, simply and efficiently, in predetermined desired volumes.

It is another object of this invention to provide means and methods in accordance with the preceding object which can be used to dilute sample fluid and to dispense such fluids with high accuracy and precision in apparatus which are mainly conventional apparatus of various types.

It is still another object of this invention to provide means and methods in accordance with the preceding objects which provide a single size disposable tip which can be used for a variety of different, predetermined volume applications and which tip can be used in a manner to prevent contamination of a sample with subsequent materials handled in the means and method.

According to a preferred method of this invention, required amounts of a liquid are metered and dispensed by the use of an aspiration tip defining a tip chamber having a predetermined total volume interconnected with an aspiration probe carrying a conduit which is interconnected with a probe liquid volume. A selected amount of probe liquid is flowed from the probe liquid volume through the conduit in the probe to fill a preselected volume of the tip chamber less than the total volume. A portion of the probe liquid is aspirated and a predetermined first volume of first liquid to be metered is aspirated along with it and the first liquid is dispensed. Preferably, the aspirating step is carried out with an air gap separating the first liquid and the probe liquid, and the probe liquid is flowed into the chamber from the probe in a measured amount. In some case, an air gap can separate the aspirated probe liquid from the probe tip. Similarly, in some cases the probe liquid and first liquid are dispensed together. Each of which has been accurate and precisely measured within the aspiration tip chamber. Preferably a single size aspiration tip can be used to aspirate different volume sample of liquid and/or different volumes of reagent and/or different volumes of a flush liquid such as water.

Apparatus for metering and dispensing required amounts of liquid comprises means defining a tip chamber having a predetermined total volume interconnected with an aspiration tube carrying a conduit which is interconnected with a probe liquid volume. The apparatus has means for flowing a selected amount of liquid from the probe liquid volume through the conduit in the probe, to fill a preselected volume of the chamber less than the total volume, and means for aspirating a portion of the probe liquid and a predetermined first volume of first liquid to be metered. Means are provided for dispensing the first liquid with or without the probe liquid. Means are provided for creating an air gap separating the first liquid and the probe liquid.

It is a feature of this invention that a single tip having a tip chamber volume of predetermined size, can be used to hold two largely different volumes of a sample and/or sample and reagent. The apparatus and probe can provide a filler liquid which can be a neutral liquid such as a flushing or cleaning liquid or an actual reagent for use with the sample to be metered and dispensed. In all cases, air gaps can provide spacing and isolation of different liquids held in the tip. Because there may be some intermixing of two fluids, even if separated by an air gap, although this is doubtful, the use of disposable tips can further aid in preventing contamination of the apparatus and probe used. Good isolation of the central apparatus and probe from a sample to be tested, as well as between any one sample and subsequent samples to be tested, can be achieved with dispensing of predetermined amounts of liquids with high accuracy and high precision in a simple and efficient mechanism. Often the apparatus used can be conventional metering and diluting equipment provided with suitable software or automatic instructions, or even manual operative instructions to provide the mechanism and methods of the present invention.

BRIEF DESCRIPTION OF THE DRAWINGS

The above and other objects, features and advantages of the present invention will be better understood from a reading of the following Specification in conjunction with a viewing of the drawings in which.

DESCRIPTION OF PREFERRED EMBODIMENTS

Figure 1:
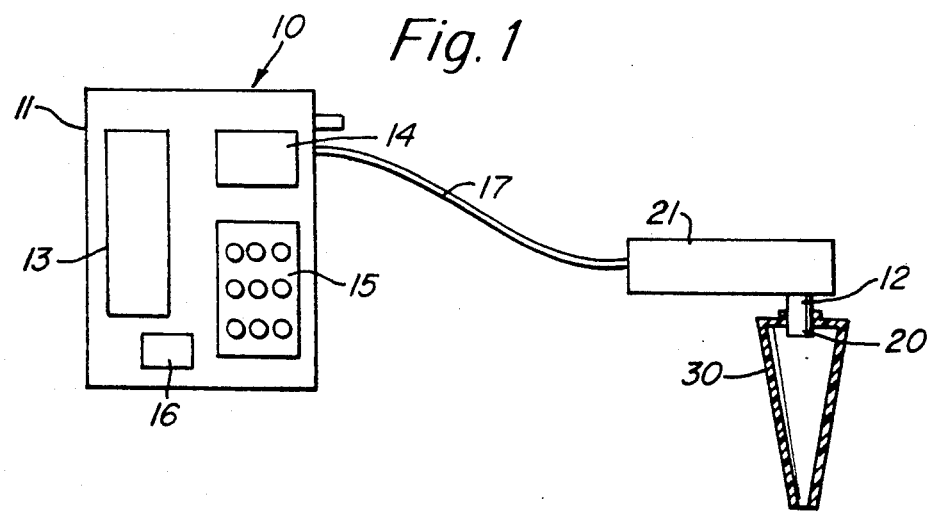
FIG. 1 is a semidiagrammatic front view of a measuring and dispensing apparatus in accordance with a preferred embodiment of this invention.

With reference now to the drawings, and more particular FIG. 1, a diluter/dispenser of conventional type is illustrated generally at 10 in FIG. 1 and has a body section 11 with a probe 12 which can be hand held.

The body section has a metering pump 13 which can be of any conventional type, a read out 14 and a keyboard 15 enabling one to select any program of metering and dispensing that has been programmed into the machine, which program can be read out at the indicator means 14. The diluter/dispenser apparatus is sometimes known as a pipetter or diluter/dispenser apparatus and often devices of this type can be used for measuring or metering predetermined amounts of a sample fluid by aspirating liquids through the tip of a probe 12.

Often the aspiration is provided for by metering pump 13 which can be preset by the keyboard 15 to aspirate predetermined volumes which may, for example, be from 1 microliter to 1 mililiter or higher, with high precision and accuracy. Such metering pumps are well known in the art and are of various different constructions. They can provide the dilution as well as measuring, as for example as set forth in U.S. Pat. No. 4,941,808, issued Jul. 17, 1990, which is incorporated herein by reference. Typical software gives a choice of volumes to be taken up by the probe tip 12 or dispensed from a central supply of probe liquid, as for example in a liquid probe volume tank 16 within the apparatus 10.

The probe liquid volume tank 16 can be directly connected by suitable switching of conventional type not shown to tubing 17. The pump and liquid supply 16 can be interchangably connected or both connected with the tubing 17 to allow the probe tip 12 to dispense liquid from the tank 16 or to aspirate liquid through the probe ending 20. A handle 21 allows the user to manually hold the probe so that it can be dipped in samples to be aspirated or reagent to be aspirated. The liquid within the tank 16 can be reagent liquid or a flushing solution for flushing the probe 12.

A typical known diluter/dispenser product useful as the apparatus 10, in accordance with this invention, can be a product known as Microlab 1000 offered for sale by Hamilton Company of Reno, Nevada. Such diluter/dispenser products often have a volume capacity range of from 1 microliter to 25 mililiters with precision of 0.4% to an accuracy of 1%, with final resolutions of 0.1% of syringe drive in a two syringe measuring and metering pump apparatus. Operating spring speeds of from 1 to 20 seconds per syringe stroke are common and the device can be powered by a conventional 110/115/220/240 VAC 50/60 HZ motor. High resolution stepper motors can be used to drive precision ball screws of known construction. The controller memory for the keyboard can have as many addressable programs as required, preferably with a backup battery for storage of these programs as known in the art.

Figures 2, 3A, 3B:
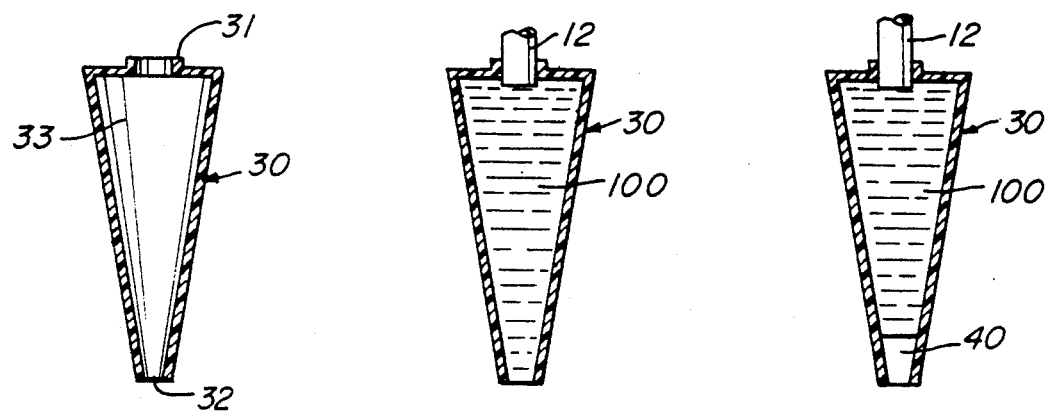
FIG. 2 is a semidiagrammatic cross section through a metering aspirating tip in accordance therewith.
FIG. 3A-3D discloses steps in a preferred method of this invention.

FIG. 2 shows a cone shaped aspiration tip 30, preferably made of a plastic material and disposable due to its relatively low cost. Aspiration tips of this type are known in the art and have means 31 of various types, such as a resilient collar, to resiliently and detachably connect with the probe 12, with a lower end 32 through which liquids can be aspirated. The tip defines a tip chamber 33. The tip itself can be of any preferred geometric shape, usually providing a lower end 32 of tubular shape and small size with a chamber 33 which is preferably of conical shape as shown. The specific attachment means to the probe can be bayonet joints, resilient collars, or any conventional known connectors enabling rapid connection and disposal with a preferably air-tight seal.

In prior art usage, when the tip 30 is connected to the probe 12, as shown in FIG. 1, the metering pump can be activated to provide an aspiration for a reagent, followed by a sample, or a sample alone, or a reagent alone. Because of the volume of the chamber 33, it is preferred to design the tips to be of a volume close to the liquid volume to be handled. For example, if the apparatus 10 is to handle a sample size of 10 microliters of a biological sample to be tested, and that sample size is to be reacted with a liquid reactant of 50 microliters, the chamber 33 might perhaps be designed to have an overall volume of 70 microliters. Thus, the probe, as shown in FIG. 1, can be positioned with the tip 32 in a reactant vessel to aspirate 50 microliters of reactant, an air gap can be left in the tubular end 32 and a sample of 10 microliters then aspirated. The 60 microliter fluid with the separating air bubble can then be dispensed by positive pumping of air from the pump 13.

In some cases, a small sample is aspirated, as for example, 10 microliters and the liquid within the tank 16 is, in fact, the reagent which is pumped through the probe and dispensed in predetermined amount, along with the sample.

It will be seen that the volume of chamber 33 can have an effect on precision and accuracy when aspiration is used. For example, if one wishes to aspirate a predetermined, smaller amount than the chamber size, the volume of air between the sample of fluid or liquid intake and the probe tip of 12 should be maintained small, in order to aid in precision. Similarly, when dispensing, or flowing a fluid from the tank 16 into the chamber, the smaller the volume of air dealt with, the less the effect of the compressibility of air or other gas within the chamber will have on the preciseness and accuracy of the measurement.

The prior art has turned to using different sized aspiration tips when different volumes of samples are to be metered and dispensed. Thus, it is not uncommon for an apparatus 10 to be provided with changeable probes 12 to allow tips of, for example, 50 microliter chamber 33 size and 150 microliter chamber 33 size to be attached to the probe 12. The use of plural size tips can cause problems with storage, increase cost and is less desirable than if a single sized disposable tip could be used.

By the means and method of this invention, the apparatus 10 is caused to operate, by suitable programming or otherwise, so that only a single size chamber 33 volume tip can be used for a variety of sample sizes.

According to a preferred embodiment of this invention, for metering and dispensing, as best shown in FIG. 3A-D, a flushing fluid such as water, is mounted in the probe liquid tank 16. The apparatus 10 is programmed and the program is selected by the keys 15 so as to carry out the steps as described below. A 150 microliter chamber 33, in an aspiration tip 30, which is of a disposable plastic such as a clear acrylic is used. In a first step (FIG. 3A) liquid 100 from the probe and tank 16 is flushed into the chamber 33 to fill the chamber. In a next step, the flush solution which may be, for example, water in an amount of 140 microliters is aspirated as shown in FIG. 3B, to provide an air gap of, for example, 10 microliters at 40. Further aspiration is carried out in the presence of a reagent at tip 32 to aspirate a 100 microliters of a reagent shown at 41. The tip is then placed in a sample and a 5 microliter sample is aspirated at 42, leaving a -5- microliter air gap 43. In this example, air gaps 40 and 43 clearly separate the flush solution from the reagent and the reagent from the sample 42, respectively, to provide for prevention of contamination. Because of the air gap 40, the likelihood of contamination of the apparatus 10 is substantially eliminated, although it is always possible that some contamination could occur. However, upon metering precisely and accurately, both the reagent, the sample and the flush in addition to the position shown in FIG. 3D, the pump of the apparatus 10 is applied to disburse the reagent and sample into a preselected area such as a test tube, the aspirating tip moved to a disposal area and the flush solution is then flushed by the pump to completely clear the tip.

The tip itself can be discarded at this point, if desired, and another tip 30 of similar size used to dispense a different size sample.

Figures 3C, 3D, 4:
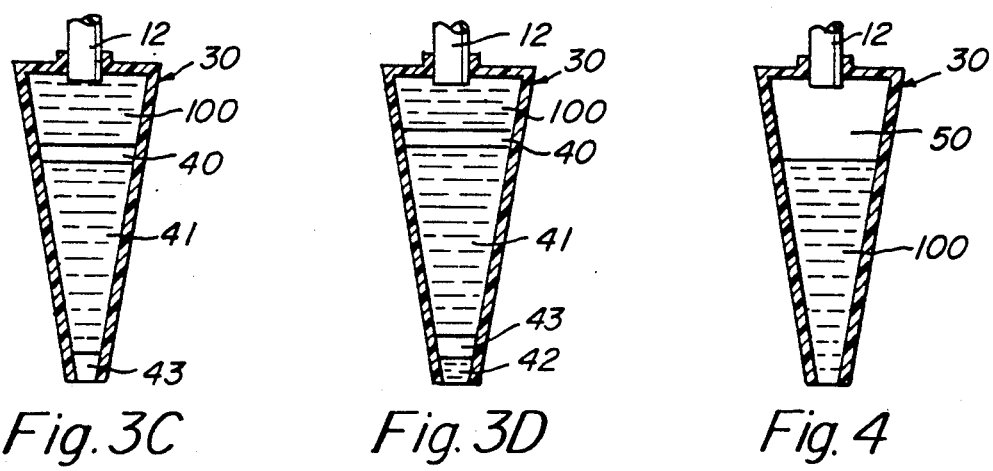
FIG. 4 illustrates a second series of steps in accordance with another method of this invention.

When using a tip 30 with a chamber 33 of 150 microliters, the filled chamber in FIG. 3D can comprise a larger amount of flush liquid 100, the same amount of reagent, the air gap volumes and a sample size of only 10 microliters. Here, although the sample size is smaller, the chamber volume is substantially filled with liquid.

In still another embodiment of this invention, rather than backflow the flush material directly into the tip to completely fill the chamber 33 and work from there, in a first step, the flush solution 100 or other probe liquid is flowed into the chamber 33, leaving an air gap 50 of small volume between the flush 100 and the tip end 31. This further insulates the probe and apparatus 10 against contamination. All steps as previously described are then used to aspirate first the reagent with an intermittent air gap and then a sample with an intermittent air gap. The reagent and sample are then dispensed, preferably the apparatus flushed, and the sample aspirating tip disposed of. In some case, the aspirating tip can be re-used.

While a specific example of method steps and sequences has been shown and described, many variations are possible. For example, the probe liquid in the container 10 and supplied through the probe 12 can be a reagent or flush material. When the probe liquid is a reagent, the method of forming the air gap 50 illustrated in FIG. 4 is preferred. The flush material can be water, alcohol or any other material. When the flush material is in fact a reagent, it can serve both a reagent and flush material function.

The specific size and geometry of the disposable tip can vary greatly. While the flush or reagent can be provided by the apparatus 10, the reagent, and in some cases the flush, can be provided by aspiration from an outside source, as can the sample. While the tip is preferably disposable, because of the use of the air gap and flush techniques, in some cases non-disposable tips can be used, along with non disposable chambers.

The specific form of attachment of the tip to the probe can vary greatly, as previously described. Suitable combinations of flush reagent and sample for various tests are shown in Table 1 below.

In all forms of the invention, high accuracy and precision can be obtained, as for example, 2% precision when metering volumes of from 5 microliters to 1 milliliter.

| FLUSH MATERIAL | REAGENT MATERIAL | SAMPLE MATERIAL TEST |
|---|---|---|
| Normal Saline | Buffered Enzyme Solution | Human Serum |
| Distilled H2O | Solution | Human Plasma |
| Dilute Surfactant | Buffered Antibody Coupled Enzyme Solution | Human Blood |
| Buffered Solution | Buffered Antibody Solution | Human Urine Animal Serum/ Plasma/Blood Human Cerebral Spinal Fluid Saliva |

In all cases, it is preferred to have a backflow from the probe to fill a volume within the aspirating tip with a liquid to reduce the gas within that tip and thus allow for more precise and accurate measurement and flow of liquids within the tip.

It should be noted that the same sized tip can be used to dispense precise and accurate small or large samples, as long as the extra space, when there is extra space, is filled with an incompressible liquid.

What is claimed is:

1. A method of metering and dispensing required amounts of liquid by the use of an aspiration tip defining a tip chamber having a predetermined total volume, interconnected with an aspiration probe carrying a conduit which is interconnected with a probe liquid volume available from a reservoir, said method comprising flowing a selected amount of probe liquid from said probe liquid volume through said conduit in said probe to fill a preselected volume of said chamber with probe liquid, less than said total volume, but of a volume large enough to substantially fill said chamber along with supplemental liquid to be used in said chamber, aspirating a portion of said probe liquid and a predetermined first volume of first liquid to be metered; and, dispensing said first liquid.

2. A method of claim 1, wherein said aspirating step is carried out with an air gap separating said first liquid and said probe liquid.

3. A method of claim 2, and further comprising aspirating a second liquid.

4. A method of claim 3, wherein said first liquid is a test reactant and said second liquid is a sample.

5. A method of claim 1 and further comprising dispensing said probe liquid and first liquid.

6. In a method of metering and dispensing a first liquid using a probe having an aspiration tip defining a tip chamber, the improvement comprising, sizing said aspiration tip chamber so as to be capable of holding and metering two largely different volumes of said first liquid, and introducing a filler liquid into a portion of said chamber and aspirating a predetermined amount of said first liquid into said chamber, whereby a predetermined amount of said first liquid can be metered and dispensed with high accuracy and precision.

7. A method of claim 6, wherein said aspirating step is carried out with an air gap separating said first liquid and said filler liquid.

8. The method of claim 7, wherein said filler liquid is a reagent capable of reacting with said first liquid.

9. The method of claim 6 wherein the improvement further comprises aspirating a second liquid into said chamber tip with an air gap between said second liquid and said first liquid.

10. The improvement of claim 9, wherein said first liquid is a reagent capable of reacting with said second liquid.

11. The method of claim 9, and further comprising dispensing said first and second liquid, and
   removing said aspiration tip from said probe and discarding said aspiration tip.

12. The improvement of claim 11, and further comprising mounting a second aspiration tip substantially identical to said first aspiration tip on said probe, said second aspiration tip being of a different size than said first aspiration tip, and repeating said introducing and aspirating, wherein said first liquid aspirated into said second replaced aspiration tip is in a predetermined amount different than the predetermined amount aspirated into said first aspiration tip.

13. The method of claim 6, wherein the improvement further comprises dispensing said first liquid.

* * * * *